United States Patent
Rothenwaender et al.

(10) Patent No.: US 8,324,765 B2
(45) Date of Patent: Dec. 4, 2012

(54) FLUID-OPERATED MEDICAL OR DENTAL HANDLE WITH SPEED LIMITING

(75) Inventors: Michael Rothenwaender, Lamprechtshausen (AT); Christoph Kment, Vienna (AT); Juergen Koelndorfer, Vienna (AT); Wilhelm Brugger, Wals-Siezenheim (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 424 days.

(21) Appl. No.: 12/547,405

(22) Filed: Aug. 25, 2009

(65) Prior Publication Data
US 2010/0055642 A1 Mar. 4, 2010

(30) Foreign Application Priority Data
Aug. 26, 2008 (EP) .................................. 08015004

(51) Int. Cl.
*H02K 7/14* (2006.01)
*A61C 3/00* (2006.01)
*A61C 1/04* (2006.01)
(52) U.S. Cl. ............... 310/50; 310/47; 433/32; 433/132
(58) Field of Classification Search .................... 310/50, 310/47; 433/32, 132
See application file for complete search history.

(56) References Cited

U.S. PATENT DOCUMENTS

| 3,091,033 | A | * | 5/1963 | Ellman | 433/86 |
| 3,109,238 | A | * | 11/1963 | Marks | 433/131 |
| 3,578,872 | A | | 5/1971 | McBurnie | |
| 3,731,384 | A | * | 5/1973 | Brooks et al. | 433/32 |
| 4,546,305 | A | * | 10/1985 | Goddijn et al. | 323/299 |
| 4,727,321 | A | * | 2/1988 | Huschelrath | 324/226 |
| 4,820,964 | A | * | 4/1989 | Kadah et al. | 318/786 |
| 4,910,444 | A | * | 3/1990 | Kilstrom et al. | 318/375 |
| 5,538,423 | A | | 7/1996 | Coss et al. | |
| 2002/0011812 | A1 | * | 1/2002 | Yabe | 318/443 |
| 2004/0005528 | A1 | | 1/2004 | Jikuhara et al. | |
| 2005/0033544 | A1 | | 2/2005 | Brooks et al. | |
| 2007/0190484 | A1 | | 8/2007 | Brennan et al. | |
| 2008/0097325 | A1 | * | 4/2008 | Tanaka et al. | 604/154 |

FOREIGN PATENT DOCUMENTS

GB 2188790 A * 10/1987

OTHER PUBLICATIONS

European Search Report for EP 08 01 5004 (mailed Mar. 13, 2009).

* cited by examiner

*Primary Examiner* — Quyen Leung
*Assistant Examiner* — Jose Gonzalez Quinones
(74) *Attorney, Agent, or Firm* — Klarquist Sparkman, LLP

(57) ABSTRACT

A fluid-operated medical or dental handle with a device for limiting the rotational speed to a maximum rotational speed value is disclosed. The handle comprises a rotating part that can be induced to rotation by a driving fluid for driving a tool connectable to the rotating part, an electrodynamic transducer driven by the rotating part for induction of an electric voltage, wherein the electrodynamic transducer has at least one coil and a magnetic element and at least one switch element for optional opening and closing of a circuit between the two ends of the at least one coil, so that with the circuit closed, an electric current and an induced magnetic field that decelerates the rotational speed of the rotating part and the tool connectable thereto can be induced in the coil of the electrodynamic transducer.

22 Claims, 3 Drawing Sheets

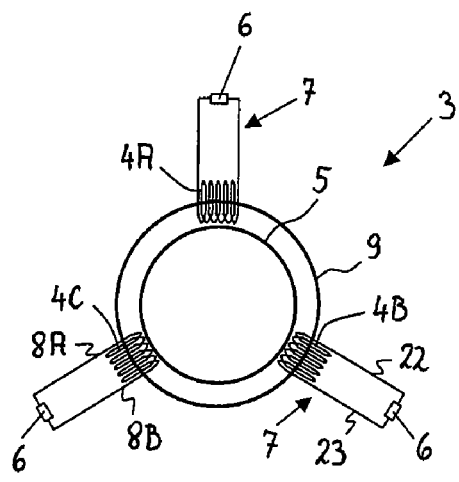
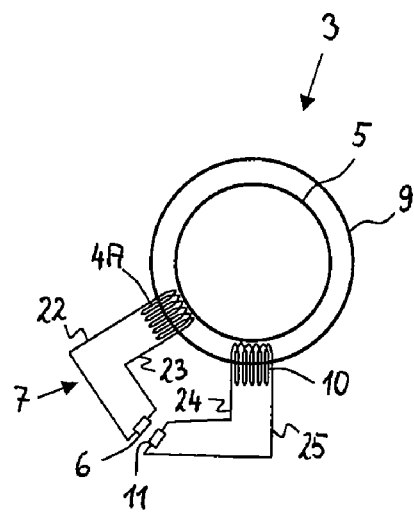
FIG. 3
FIG. 5
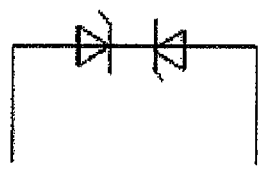
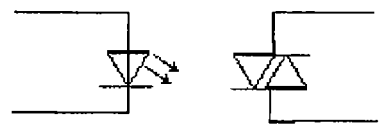
FIG. 4A
FIG. 4B
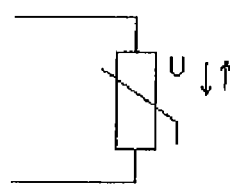
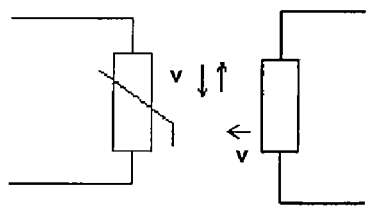
FIG. 4C
FIG. 4D

FLUID-OPERATED MEDICAL OR DENTAL HANDLE WITH SPEED LIMITING

CROSS REFERENCE TO RELATED APPLICATION

The present application claims priority from pending European Patent Application No. 08015004.8 filed Aug. 26, 2008, which is incorporated herein by reference.

BACKGROUND

1. Field

This application relates to a fluid-operated medical or dental handle with a device for limiting rotational speed and a method for limiting the rotational speed of such a handle.

2. Description of Prior Art

U.S. Pat. No. 3,578,872 discloses such a fluid-operated handle with a device for limiting rotational speed. To this end, a U-shaped receptacle that rotates with the rotor is provided on the handle, an elastic O-ring being provided in the receptacle. On the outside edge of the end facing away from the rotor, the U-shaped receptacle has a plurality of openings. With an increase in rotational speed, the elastic ring expands due to centrifugal force and partially covers the openings, thereby reducing the throughput of propellant air through the openings and also through the rotor. The rotational speed of the handle is thus limited by the change in the effective cross section of the line of driving fluid.

One of the disadvantages of this device for limiting rotational speed is that the O-ring loses its elasticity due to aging of the material and external influences, so that as a consequence the device for limiting rotational speed will continue to function only to a limited extent or not at all.

In addition, several nongeneric handles with rotational speed regulation are known from the prior art, e.g., as shown in U.S. Patent Publication No. US 2007/0190484 A1. These handles comprise a closed loop with a rotational speed sensor for determining an actual rotational speed value of a tool or an impeller, a controller for comparing the actual rotational speed value with a set rotational speed value and an actuator, often a control valve, by means of which the volume flow of the driving fluid can be varied. The design of these handles with the closed loop is complex and expensive and their operational performance is often unstable.

One problem that remains to be solved is therefore to create a fluid-operated medical or dental handle with a speed limiting device, which does not have the disadvantages of the speed limiting device from U.S. Pat. No. 3,578,872.

SUMMARY

According to one embodiment, this problem is addressed by a fluid-operated medical or dental handle which comprises a rotating part which can be induced to rotation by a driving fluid for driving a tool which can be connected to the rotating part and an electrodynamic transducer driven by the rotational part for induction of an electric voltage. The electrodynamic transducer comprises at least one coil and one magnetic element. The handle also contains at least one switch element for optional opening and closing of the circuit between the two ends of the at least one coil, so that with the circuit closed in the coil of the electrodynamic transducer—by the induction voltage generated by the electrodynamic transducer—an electric current and an induced magnetic field retarding the rotational speed of the rotating part and the tool connectable thereto can be induced.

One advantage of the handle and in particular of the speed limiting device comprising the electrodynamic transducer and the switch element is that for limiting rotational speed and in particular for creating the braking force for retarding the rotational part, no mechanical components that are susceptible to wear are required. The braking effect is achieved by electrodynamic effects, in particular by induction, wherein a voltage is induced in the coil of the electrodynamic transducer by rotation of the rotor of the electrodynamic transducer. If the two ends of the coil are joined by the switch element, then an electric current flows through this coil, so that this induced current induces the formation of a magnetic field, which is referred to below as an induced magnetic field. This induced magnetic field counteracts the cause of the induction, i.e., the magnetic field of the magnetic element of the electrodynamic transducer, and thus decelerates the rotor of the electrodynamic transducer and the rotational part and tool of the handle connected thereto. The decelerating effect is based on the principle of Lenz's rule, which is familiar to those skilled in the art, so that no further discussion is required here.

The speed limiting device limits the rotational speed of the rotating part and of the tool to a maximum value, in particular at a low load or in idling of the handle, to thereby reduce the noise emission by the handle and to reduce the mechanical burden of the ball bearings which are provided in the handle and support the rotating part. The speed limit also allows the tool to be set down more gently on the treatment site. According to one embodiment, the switch element limits the rotational speed of the rotating part and the tool connectable to it to a value in the range from approximately 300,000-150,000 rpm (revolutions per minute), preferably to a value in the range of approximately 275,000-200,000 rpm, especially preferably to approximately 250,000 rpm.

Through the choice of switch elements with different switching values, it is also possible to implement speed limits with different maximum rotational speeds in such handles.

The electrodynamic transducer, hereinafter also referred to as a generator, has a stator and a rotor, wherein the rotor is connected to the rotating part or is designed as part of the rotating part. The rotating part includes, for example, the impeller of the handle, which is acted upon by the driving fluid, a shaft rotatably mounted in the handle, e.g., a hollow shaft for releasably securing the treatment tool or the shaft of a tool that can be accommodated in the handle. The rotor preferably comprises the magnetic element and the stator preferably comprises the at least one coil but of course the inverse of this design is also possible. The magnetic element is especially preferably designed as a permanent magnet, which is attached to the rotating part as a discoidal magnet in particular. Alternatively, the rotating part itself is magnetic, e.g., due to being manufactured from magnetic material or by magnetization.

The switch element or parts thereof connect the two ends of the at least one coil of the generator, preferably made of copper wire, and/or short-circuit it. At least parts of the switch element are thus part of the circuit which optionally also comprises, in addition to the coil of the generator, other electric or electronic components, e.g., electrically conducting wires or an electric load.

The switch element closes the circuit on reaching or exceeding a switching value or a switch range. The voltage induced by the electrodynamic transducer and/or a parameter that depends on the voltage serves to trigger the switch, wherein the induced voltage is directly proportional to the rotational speed of the rotating part or the tool. For example, if the induced voltage reaches the predetermined switching value (the so-called switching voltage or conducting-state voltage) of a diode, which serves as a switch element, then it switches through, i.e., it is put in a low-resistance state, so that a high electric current flow is possible through the diode and thus through the coil of the electrodynamic transducer. If the switch element comprises an electric resistor, for example, then the current flow begins less abruptly in comparison with the diode, so that here after exceeding a switching value there is a switch range in which, depending on the induced voltage of the generator, the electric current flow increases. Alternatively, it is also possible for the switch range to be formed by multiple switching values. For example, this is achieved by the fact that the switch element comprises several switch units or switches which can be activated sequentially with an increasing induced voltage.

According to one embodiment, the at least one coil is wound around a soft magnetic coil core, which concentrates the magnetic flux of the magnetic element of the generator and directs it to the coil. The soft magnetic coil core consisting of one or more layers, preferably insulated electrically from one another, is ring shaped in particular and surrounds the magnetic element on its outside circumference. Thus when the electrodynamic transducer comprises multiple coils in particular, their installation in the handle is facilitated.

By providing multiple coils, preferably three, an increased braking effect is achieved. Especially if the coils are preferably arranged essentially uniformly around the magnetic element, then quiet running of the rotating part and the tool in braking is impaired only slightly or not at all. According to a preferred embodiment, each coil is connected to a switch element, wherein these switch elements have the same or similar switching values, so that essentially simultaneous induction of the induced magnetic fields is possible. Due to the same or similar switching values, uniform deceleration of the rotating part and the tool is additionally supported. Alternatively, each coil is connected to a switch element, which have different switching values, so that sequential induction of the induced magnetic fields can be implemented.

The switch element may comprise any known switch, in particular any electric or electronic switch. According to one embodiment, the switch element comprises one or more semiconductor diodes, in particular thyristors, e.g., two Zener diodes in anti-serial arrangement, a two-directional diode (diac) or an electromagnetic light-emitting diode (LED) and a semiconductor element that receives the radiated light, e.g., a photodiode, a phototransistor or a photo triac, a photo relay, a MOS-FET relay, a semiconductor relay or a solid-state relay. Among other things, the advantage of using semiconductor diodes consists of the fact that no other components except one or two diodes are needed for the switch function.

According to an alternative embodiment, the switch element comprises at least one electric resistor, in particular a voltage-dependent resistor or a temperature-dependent resistor. The advantage of using resistors in comparison with semiconductor diodes is their greater robustness and their greater resistance to external influences such as elevated temperatures.

According to another embodiment, the electrodynamic transducer has at least one control coil in which an electric voltage and an electric current are also induced. However, the control coil is not provided with a switch element like the other coils, which are referred to as brake coils for differentiation and which generate the induced magnetic field which decelerates the rotating part, but instead it is connected to an electric consumer or is operatively connected to a sensor. A consumer, e.g., a light-emitting diode or a heating element, are parts of the switch element or are operatively connected thereto in order to trigger the switch function.

For example, the sensor is provided to measure a parameter of the voltage induced in the control coil or of the induced current flowing between the ends of the control of coil, in particular the frequency of the induced alternating voltage, and to send a signal corresponding to the measured value to a control unit having an electronic circuit or a microcontroller. The control unit or the microcontroller is connected to the at least one switch element of the brake coil or is part of the switch element and opens or closes the circuit connecting the ends of the brake coil, based on the sensor signal, by activation or deactivation of the switch element. The switch element may be designed as an electric, electronic or mechanical switch element.

According to one embodiment, it is of course also possible to additionally connect an electric consumer, which is not part of the switch element to the control coil. Preferably a radiation source for emitting visible radiation for illuminating the preparation site, in particular at least one light-emitting diode, can be connected to the control coil. The light emitted by the radiation source is delivered to the preparation site either directly or via a waveguide. Other electric consumers connectable to the control coil comprise, for example, a diode laser, sensors, in particular sensors for measuring the temperature, the rotational speed or the torque, actuators, in particular piezoelements for vibration damping, circuits for processing or evaluating of data or measured values, control and/or regulating circuits, transmitters, displays, screens or devices for detecting tools, instruments or other components that can be connected to the handle.

According to another embodiment, the electrodynamic transducer and the entire switch element are accommodated in the handle, thereby greatly improving the ease of handling the handle.

A method for limiting the rotational speed of the medical fluid-operated handle, in particular a dental handle as described herein, is characterized in that a voltage is induced in the at least one coil of the electrodynamic transducer by rotation of the rotating part, and the switch element closes a circuit between the two ends of the at least one coil on reaching or exceeding the switching value of the switch element, so that in the coil of the electrodynamic transducer an electric current and an induced magnetic field are induced, wherein the induced magnetic field decelerates the rotational speed of the rotating part and the tool connectable thereto.

Various embodiments, including preferred embodiments, are described in greater detail below with reference to the accompanying drawings.

BRIEF DESCRIPTION OF THE DRAWINGS

FIG. 3 shows a schematic diagram of an embodiment of a device for limiting the rotational speed, wherein the electrodynamic transducer comprises three induction coils.

FIGS. 4A-4D show various embodiments of the switch element of the device for limiting the rotational speed.

FIG. 5 shows a schematic diagram of an embodiment of a device for limiting the rotational speed, wherein the electrodynamic transducer has a control coil and a brake coil for generating an induced magnetic field decelerating the rotating part.

DETAILED DESCRIPTION

Figure 1:
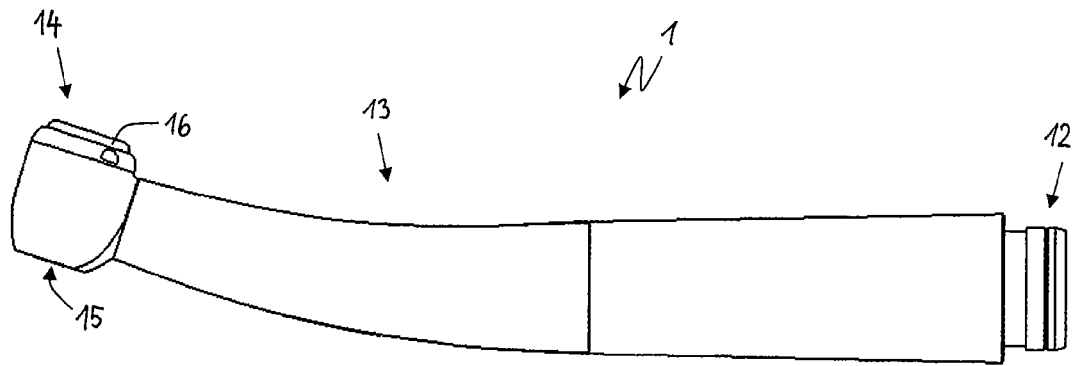
FIG. 1 shows an embodiment of a medical, in particular a dental, fluid-operated handle with a device for limiting the rotational speed.

The fluid-operated medical, in particular dental, handle 1 shown in FIG. 1 is designed as an elongated tubular instrument having a connection 12 to a fluid source, in particular a compressed air source, on its first end. The handle 1 comprises a handle part 13 that is curved or has two sections arranged at an angle to one another, and a head part 14 connected thereto. A tool opening 15 through which a tool is detachably insertable into the head part 14 is provided on the head part 14. The tool opening 15 is arranged on a side of the head part 14, so that the tool protrudes out of the head part 14 at an angle to the handle part 13 or its longitudinal axis. A pushbutton 16 cooperating with a tool release mechanism arranged in the head part 14 is provided on the end of the head part 14 opposite the tool opening 15 to release the tool from the head part 14. The handle 1 may of course have other known shapes, e.g., it may be designed to be straight or pistol-shaped.

At least one fluid line for the driving fluid extends from the connecting device 12 in the direction of the head part 14. Additional media lines, e.g., one or more media lines for cooling media, waveguides or electric lines, optionally extend from the connecting device 12 through the handle 1. The fluid line conveys the driving fluid, e.g., compressed air or water, to a drive unit, comprising at least one rotating part 2 which can be induced to rotate, e.g., an impeller, a rotor of an air motor or a rotating piston air engine, a shaft, a chucking device for the tool, etc.

Figure 2:
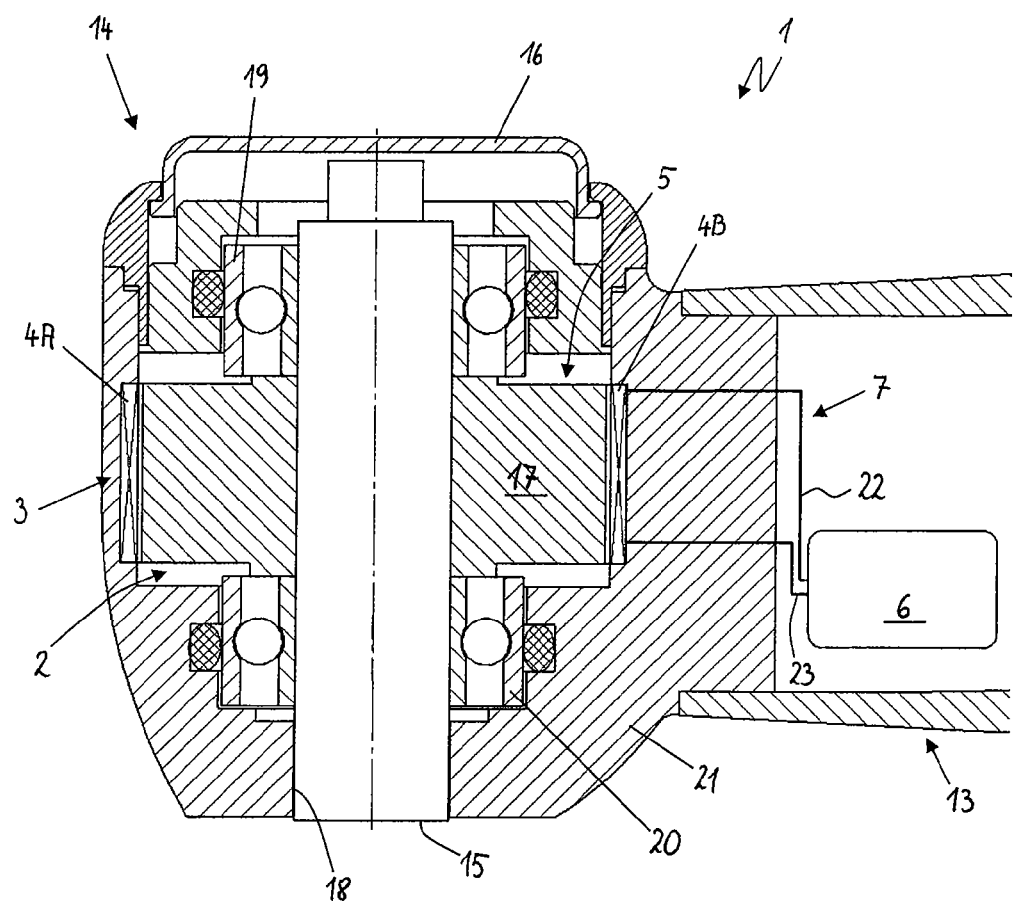
FIG. 2 shows a sectional diagram of the head part of the handle of FIG. 1 with the device for limiting the rotational speed, comprising an electrodynamic transducer and a switch element connected to the transducer.

According to the embodiment of the handle 1 shown in FIG. 2, the rotating part 2 comprises the impeller 17 and a hollow shaft 18 on which the impeller 17 is mounted and in which the chucking device for the tool is arranged or which is part of the chucking device. The rotating part 2 and the tool connectable thereto are supported rotatably in the handle 1 by two roller bearings 19, 20. The roller bearings 19, 20 are supported on rotationally fixed components of the handle 1, e.g., the outer sleeve 21.

In the head part 14 of the handle 1, an electrodynamic transducer or generator 3 comprising a rotor and a stator is provided. The stator is formed by at least one coil, preferably several coils 4A, 4B, 4C and a soft magnetic coil core 9 (FIG. 3), around which the coils 4A, 4B, 4C are wound. The coils 4A, 4B, 4C and the coil core 9 surround the rotor having a magnetic element 5. The rotor according to FIG. 2 comprises the at least partially magnetic impeller 17, the vanes of the impeller 17 preferably being magnetic as a result of magnetization.

By acting upon the impeller 17 with the driving fluid and by inducing rotation of same, the electrodynamic transducer 3 is thus activated and a voltage is induced in the coils 4A, 4B, 4C. The level of the voltage induced in the coils 4A, 4B, 4C is directly proportional to the rotational speed of the rotor, the rotating part 2 and the tool. The coils 4A, 4B, 4C are connected to the switch elements 6 via their ends 8A, 8B (see FIG. 3) and via electric lines 22, 23.

The switch elements 6 are switchable between a first state, which is open, and in which the connection between the ends 8A, 8B of the coils 4A, 4B, 4C is interrupted, and a second state, which is closed, and in which the ends 8A, 8B are connected to one another. In this second state, electric current flows due to the induced voltage through the circuit 7 formed by the coils 4A, 4B, 4C, the lines 22, 23 and the switch element 6. Switching from the open first state, which is the basic state of the switch element 6, into the closed state occurs as a function of the level of the induced voltage. Electric current thus flows through the circuit 7 and in particular the coils 4A, 4B, 4C when the rotational speed of the rotating part 2 is high enough to induce a voltage that reaches or exceeds the switching value of the switch element 6. If the induced voltage drops below the switch level due to the low rotational speed of the rotating part 2, then the switch element 6 automatically returns to its basic state.

As already mentioned above, the induced current flowing through the coils 4A, 4B, 4C triggers the development of an induced magnetic field in the coils 4A, 4B, 4C. This induced magnetic field counteracts the cause of induction, i.e., the magnetic field of the magnetic element 5 of the electrodynamic transducer 3, and thus decelerates the rotor of the electrodynamic transducer 3, the rotating part 2 and the tool of the handle 1. Since the induced voltage, the induced current and the intensity of the induced magnetic field increase with an increase in rotational speed, a reliable limitation on the rotational speed of the rotating part 2 and the tool to a maximum rotational speed is achieved by means of this device for limiting rotational speed.

FIG. 3 shows in a view from above the electrodynamic transducer 3 and three circuits 7, whose coils 4A, 4B, 4C are arranged essentially regularly around the magnetic element 5. Each coil 4A, 4B, 4C and each circuit 7 is assigned a switch element 6, whereby preferably the three switch elements 6 have essentially the same switching values, so that the three switch elements 6 close the circuits 7 essentially simultaneously with an increase in rotational speed and/or open them simultaneously with a drop in rotational speed and accordingly the induced magnetic fields are also induced essentially simultaneously and/or collapse essentially simultaneously.

FIGS. 4A and 4C show two possible embodiments of the switch elements 6 such as those which may be used in the circuits 7 in FIG. 3, for example. FIG. 4A shows two antiserially connected Zener diodes, which have a low resistance when their switching voltage is exceeded, so that a high electric current flows through the circuit 7 and the coils 4A, 4B, 4C. FIG. 4C shows a voltage-dependent resistor, whose resistance value drops with an increase in the induced voltage, so as a result, a high electric current flows through the circuit 7 and the coils 4A, 4B, 4C.

FIG. 5 shows an alternative embodiment of a device for limiting rotational speed, which in turn comprises an electrodynamic transducer 3 and a circuit 7 with a coil 4A, conductors 22, 23 and a switch element 6. These components and the components of FIG. 3 labeled with the same reference numerals have the same design and the same function. In addition, the device for limiting rotational speed according to FIG. 5 has a control coil 10, which is connected to an electric consumer 11 via electric lines 24, 25. The electric consumer 11 is assigned to the switch element 6 or is arranged opposite the switch element 6.

During operation of the electrodynamic transducer 3, a voltage which creates a current flow is induced in the control coil 10, thereby operating the consumer 11. For example, the consumer 11 may comprise one or more electromagnetic light-emitting diodes (see FIG. 4B) which emit light in the direction of the switch element 6, when the value of the voltage induced in the control coil 10 is high enough to exceed their switching value. The switch element 6 is formed by a semiconductor element receiving the radiation, e.g., a photodiode, which changes to the closed state as soon as it receives radiation emitted by the light-emitting diode, thereby closing the circuit 7, so that an induced magnetic field builds up in the coil 4A which causes deceleration of the rotational part 2, as described above.

The control coil 10 and the brake coil 4A are either arranged side by side, as shown in FIG. 5, or the two coils are wound one above the other for the purpose of saving space; in particular, the control coil 10 is wound over the brake coil 4A. According to a preferred embodiment, the control coil 10 is also connected to a rectifier to convert the induced alternating current into direct current.

FIG. 4D shows a schematic representation of the electric consumer configured as one or more heat-emitting heating elements, e.g., a heating film. Referring again to FIG. 5, the electric consumer 11 configured as the heating element is heated by the current flowing in the lines 24 and 25 and emits thermal radiation in the direction of the switch element 6, comprising a temperature-dependent resistor (NTC resistor), for example. With an increase in temperature, the resistance value of the temperature-dependent resistor drops, so that the circuit 7 is closed, current flows through the circuit 7 and the coil 4A and again an induced magnetic field, which decelerates the rotating part 2, is built up in the coil 4A.

Figure 6:
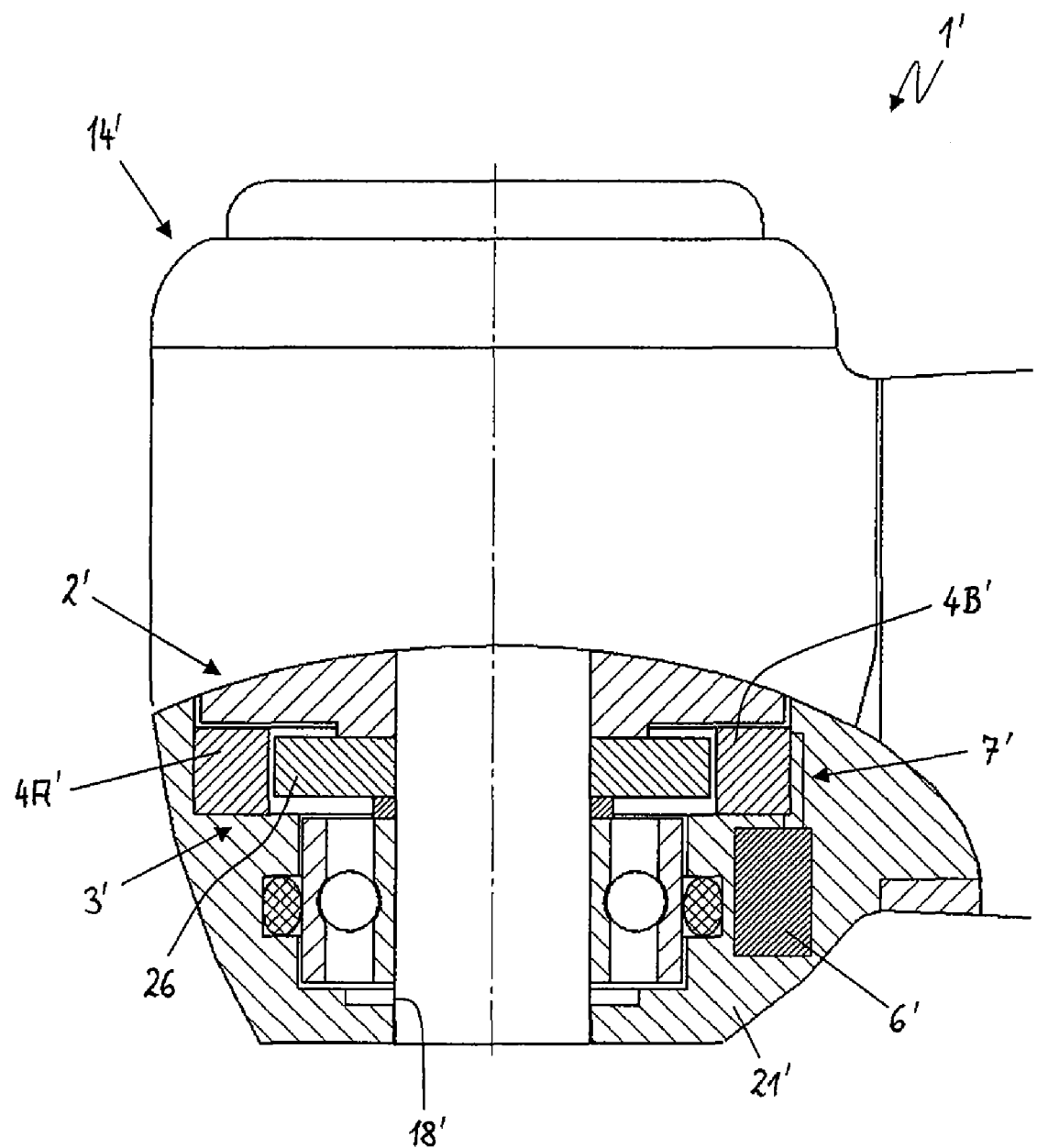
FIG. 6 shows an alternative embodiment of a head part of a medical, in particular dental, fluid-operated handle with a device for limiting the rotational speed, comprising a disk-shaped magnetic element surrounding the tool receptacle.

The head part 14' of the handle 1' shown in FIG. 6 has the same design as the head part 14 shown in FIG. 2. The difference from the head part 14 is that the magnetic element of the electrodynamic transducer 3' is designed as a disk-shaped permanent magnet 26, e.g., as a neodymium-iron-boron magnet, which is mounted on the rotating part 2', in particular on the shaft 18'. The coils 4A', 4B' surrounding the magnetic element 26 are supported on shoulders of the head housing 21'. Each coil 4A', 4B' is connected by electric lines to a switch element 6' (only one is shown) to form a circuit 7'. In contrast with the handle 1 of FIG. 2, where at least one, preferably all switch elements 6 are provided in the handle part 13, the switch elements 6' and the entire circuit 7' of the handle 1' are arranged in the head part 14'.

The embodiments described above are illustrative but not limiting, and the following claims cover all embodiments which apply or comprise the corresponding function principle(s). In addition, all features of all the embodiments illustrated and described here may be combined with one another.

What is claimed is:

1. A fluid-operated medical or dental handle comprising a rotating part that can be induced to rotate by a driving fluid for driving a tool connectable to the rotating part,
    an electrodynamic transducer driven by the rotating part for induction of an electric voltage, the electrodynamic transducer comprising at least one coil and one magnetic element, and
    at least one switch element interiorly positioned within the handle for selectively opening and closing of a circuit between the two ends of the at least one coil, so that with the circuit closed, an electric current and an induced magnetic field decelerating or limiting the rotational speed of the rotating part and of the tool connectable thereto can be induced in the coil of the electrodynamic transducer.

2. The fluid-operated medical or dental handle according to claim 1, wherein
    the magnetic element is provided on the rotating part, so that the magnetic element can be induced to rotation by the rotating part.

3. The fluid-operated medical or dental handle according to claim 1, wherein
    the at least one coil is wound around a soft magnetic coil core.

4. The fluid-operated medical or dental handle according to claim 3, wherein
    the soft magnetic coil core comprises one or more layers, is shaped in a ring and surrounds the magnetic element on its outside circumference.

5. The fluid-operated medical or dental handle according to claim 1, wherein
    the electrodynamic transducer comprises several coils.

6. The fluid-operated medical or dental handle according to claim 5, wherein
    the coils are arranged essentially uniformly about the magnetic element.

7. The fluid-operated medical or dental handle according to claim 1, wherein
    the switch element comprises one or more semiconductor diodes.

8. The fluid-operated medical or dental handle according to claim 7, wherein
    the switch element comprises two Zener diodes arranged in an antiserial configuration or a bidirectional diode.

9. The fluid-operated medical or dental handle according to claim 7, wherein
    the switch element comprises at least one electromagnetic light-emitting diode and at least one semiconductor element receiving the radiation.

10. The fluid-operated medical or dental handle according to claim 1, wherein
    the switch element comprises at least one electric resistor.

11. The fluid-operated medical or dental handle according to claim 10, wherein
    the electric resistor comprises one of a voltage-dependent resistor and a temperature-dependent resistor.

12. The fluid-operated medical or dental handle according to claim 1, wherein
    the electrodynamic transducer comprises at least one control coil, to which an electric consumer is connected or which is operatively connected to a sensor.

13. The fluid-operated medical or dental handle according to claim 1, wherein
    the switch element comprises an electronic circuit or a microcontroller.

14. The fluid-operated medical or dental handle according to claim 1, wherein
    the switch element limits the rotational speed of the rotating part and the tool connectable thereto to a value in the range of approximately 300,000-150,000 revolutions per minute.

15. The fluid-operated medical or dental handle according to claim 1, wherein
    the switch element limits the rotational speed of the rotating part and the tool connectable thereto to value in the range from approximately 275,000-200,000 revolutions per minute.

16. The fluid-operated medical or dental handle according to claim 1, wherein
    the switch element limits the rotational speed of the rotating part and the tool connectable thereto to approximately 250,000 revolutions per minute.

17. The fluid-operated medical or dental handle according to claim 1, wherein
    the electrodynamic transducer and the entire switch element are accommodated in the handle.

18. The fluid-operated medical or dental handle according to claim 1, wherein
    multiple switch elements are provided with different switching values, so that the induced magnetic fields are sequentially inducible.

19. A method for limiting the rotational speed of a fluid-operated medical or dental handle comprising a rotating part capable of connection to a tool inducible to rotate by action of a driving fluid, an electrodynamic transducer driven by the rotating part, the electrodynamic transducer comprising at least one coil and one magnetic element, and at least one switch element for selectively opening and closing a circuit between two ends of the at least one coil, the method comprising:

inducing a voltage in the at least one coil of the electrodynamic transducer by initiating rotation of the rotating part, and selectively closing a circuit between the two ends of the at least one coil with the at least one switch element, so that an electric current and an induced magnetic field that decelerates or limits the rotational speed of the rotating part and any tool connected thereto are induced in the at least one coil of the electrodynamic transducer, wherein the at least one switch element closes the circuit between the two ends of the at least one coil when the electric voltage induced by the electrodynamic transducer or a parameter that depends on said induced voltage reaches or exceeds a switching value or a switch range of the at least one switch element.

20. A fluid-operated medical or dental handle, comprising:

a rotating part that can be induced to rotate by a driving fluid for driving a tool connectable to the rotating part, an electrodynamic transducer driven by the rotating part for induction of an electric voltage, the electrodynamic transducer comprising at least one coil and one magnetic element, and at least one switch element for selectively opening and closing of a circuit between the two ends of the at least one coil, so that with the circuit closed, an electric current and an induced magnetic field decelerating or limiting the rotational speed of the rotating part and of the tool connectable thereto can be induced in the coil of the electrodynamic transducer, wherein the at least one switch element is configured to close the circuit between the two ends of the at least one coil when the electric voltage induced by the electrodynamic transducer or a parameter that depends on said induced voltage reaches or exceeds a switching value or a switch range of the at least one switch element.

21. The fluid-operated medical or dental handle according to claim 20, wherein the switch element comprises one or more semiconductor diodes.

22. The fluid-operated medical or dental handle according to claim 20, wherein the switch element comprises at least one electromagnetic light-emitting diode and at least one semiconductor element receiving the radiation of the at least one electromagnetic light-emitting diode.

\* \* \* \* \*